United States Patent [19]

Yamashita et al.

[11] Patent Number: 4,820,387

[45] Date of Patent: Apr. 11, 1989

[54] METHOD AND APPARATUS FOR MAKING THE INNER CROWNS OF COMPOSITE-LAYERED CROWNS FOR RESTORING CROWNS

[75] Inventors: Atsushi Yamashita, Okayama; Ikuo Kyotani, Kitamoto, both of Japan

[73] Assignee: G-C Dental Industrial Corp., Tokyo, Japan

[21] Appl. No.: 168,463

[22] Filed: Mar. 15, 1988

[30] Foreign Application Priority Data

Apr. 10, 1987 [JP] Japan ................................ 62-86761

[51] Int. Cl.⁴ ........................ C25D 1/00; C25D 17/00
[52] U.S. Cl. ......................................... 204/4; 204/231
[58] Field of Search ................................... 204/4, 231

[56] References Cited

U.S. PATENT DOCUMENTS 3,515,662 6/1970 Schmidt ............................. 204/231

*Primary Examiner*—T. M. Tufariello
*Attorney, Agent, or Firm*—Oblon, Fisher, Spivak, McClelland & Maier

[57] ABSTRACT

In a method and apparatus for making an inner crown of a composite-layered crown for the restoration of crowns, said inner crown being composed mainly of a noble metal, an electrically conductive coating material undissolvable in a plating bath is applied and solidified on an inner crown-forming surface of a working model of a tooth on which the state of the tooth to be restored is reproduced and which is formed of a non-conductive material, and electrical connection is made so as to render said conductive coating material cathodic, while said coating material is immersed in said plating bath; an anode is immersed in said plating bath, while said anode is fixedly located on a position opposite to said inner crown-forming position; an auxiliary electrode formed of the same metal as the metal to be plated is fixed for immersion in said plating bath between said anode and said cathode, while its one end is or is not connected to said anode and its other end is opposite and adjacent to a recess in said cathode; and a pulse current is impressed between said anode and said cathode at a pulse width of 0.01 to 50 msec. and a pulsed current density of 1 to 20 A/dm² and in a duty cycle of 1 to 30% for electroplating, thereby making said inner crown.

14 Claims, 1 Drawing Sheet

METHOD AND APPARATUS FOR MAKING THE INNER CROWNS OF COMPOSITE-LAYERED CROWNS FOR RESTORING CROWNS

BACKGROUND OF THE INVENTION

1. Field of the Invention

The present invention relates to a method for forming directly on a working model of a tooth an inner crown, primarily made of a noble metal, of a composite-layered crown for restoring crowns, which comprises an inner crown and an outer crown and is designed to be used for the restoration of crown (hereinafter simply referred to as the composite-layered crown(s)), and to an apparatus for carrying out said method.

2. Statement of the Prior Art

Heretofore, the inner crowns of the composite-layered crowns have been made by the use of either a metal casting or a metal foil. According to the method making use of a metal casting, the inner crown of the composite-layered crown is made by the precise lost-wax casting process, and according to the method making use of a metal foil, a metal foil to form the inner crown is covered over a working model of a tooth without recourse to the lost-wax casting process, then pressed against it by means of a spatula for pressing a foil, and finally swaged over that working model by a swager.

When the inner crown of the composite-layered crown is made by the use of the metal casting, a wax pattern is formed of a working model of a tooth on which the state of the tooth to be restored is reproduced (and which may hereinafter be simply called as the working model of a tooth), provided with a sprue wire, and invested in an investment. After the investment has been set, it is fired to burn out the wax pattern therein, and a molten metal is cast into the resulting void to prepare a metal casting, which is then washed, adjusted and polished. The working time required per tooth is about 30 minutes for the preparation of the wax pattern, about 1 hour for the investment thereof, about 1 hour for the burning-out thereof, about 10 minutes for casting, and about 30 minutes for the polishing of the casting. The time required for such seccessive works from the preparation of the wax pattern to the polishing of the casting thus totals up to about 3 hours. Noble and base metal alloys are generally used for such metal castings. By way of example, for fusing porcelain, on the one hand, Au-Pt-Pd and Au-Pd-Ag alloys and Ni-Cr, Ni-Cr-Mo and Ni-CrCo-Mo alloys are used as the noble and base metal alloys, respectively, and for building up plastics, on the other hand, Au-AgCu, Au-Ag-Pd and Ag-Pd alloys and Ni-Cr and Co-Cr alloys are employed as the noble and base metal alloys, respectively.

Turning to the making of the inner crown of the compositelayered crown with the use of the metal foil, a noble metal foil, which is in the form of, e.g., an umbrella with a bull's-eye design, has a thickness of 50 micrometers and is of a four-layer structure comprising 100 % Au; 85 % Au+5 % Pt+10 % Pd; 100 % Pt; and 80 % Au +10 % Pd+10 % the balance, is covered over the working model of a tooth, and is formed thereon with 8 to 10 folds with the use of a pincette. The foil is repeatedly pressed against the working model of the tooth along its surface by means of a spatula for pressing a foil. The noble metal foil is then swaged over the working model of the tooth by a swager which comprises an outer pipe and a cylindrical member to be finally fitted thereinto, has on its bottom the working model of the tooth with the noble metal foil being pressed thereagainst, and exerts a blowing and swaging action via rubber. Thereafter, the noble metal foil is taken out of the working model of the tooth, and heated with a gas burner to melt the gold in the foil.

However, the making of the inner crowns of the compositelayered crowns using the metal casting involves such problems as enumerated below.

(1) In some cases, since the dimensional accuracy of the metal casting is not so good, it may not be well-fitted over a working model of a tooth on which the state of a tooth to be restored is reproduced. This is because although the dimensional accuracy of the metal casting has to be corrected by the expansion of an investment for the reason that it is affected by dimensional changes occurring in a wax pattern, an investment and an alloy, in particular the casting shrinkage of an alloy, it is difficult to completely correct the dimensional accuracy of the metal casting due to the fact that such casting shrinkage is largely affected depending upon not only the type of alloy but also the shape of the metal casting, the strength of the investment and the casting conditions.

(2) Since the thickness of the metal casting is on the order of 200 to 300 micrometers, it is required to increase the amount of procelain or plastics to be built up so as to obtain the configuration of a crown similar to that of a natural tooth and, at the same time, obtain the color tone corresponding to that of a natural tooth. For that reason, it is required to increase the amount of a patient's tooth to be removed in the tooth preparation for fixed prosthodontics. This gives rise to an increase in the time required for the tooth preparation for fixed prothodontics to be carried out by a dentist, and causes pain to a patient. For this it is ideal to minimize the thickness of the metal casting. Actually, however, difficulty is encountered in reducing the thickness of the metal casting to 200 micrometers or less due to the occurrence of casting defects such as rounded, cold shut, rough surface and micro shrink.

(3) As already mentioned, the works from preparation, investing and burning-out of the wax pattern to the polishing of the casting takes a period of time of at least 3 hours, and the preparation of the metal casting is time-consuming to a person who carries it out.

On the other hand, the making of the inner crowns of the composite-layered crowns using a metal foil involves such problems as enumerated below.

(1) Even when a noble metal foil is covered over the working model of the tooth, is provided with 8 to 10 folds by an exclusive pincette, and is thereafter repeatedly pressed against the working model of the tooth along its surface with the use of an exclusive spatula for pressing a foil, the resulting pressed metal foil, viz., the resulting metal coping shows only incomplete fitness with respect to the working model of the tooth. For that reason, there is a certain limit in the fitness of the pressed metal foil or the metal coping with respect to the working model of the tooth, even though the pressed metal foil or the metal coping pressed against the working model of the tooth is swaged by a swager.

(2) When the pressed metal foil or the metal coping pressed against the working model of the tooth is swaged by a swager, the working model of the tooth may break down in dependence on the type, shape and size of the working model of the tooth or how to use the swager. Hence, fair experience and expertness are needed for precise swaging.

(3) When the pressed metal foil or the metal coping is removed from the working model of the tooth after it has been swaged by a swager, it tends to deform due to its limited strength. To facilitate such removal, there is a need for simplifying the preparation of the working model of the tooth, to which a dentist should pay attention in the tooth preparation for fixed prosthodontics.

(4) After the pressed metal foil or the metal coping has been removed from the working model of the tooth, it is finished up by heating with a gas burner. Although attention must then be paid to the position and time at and during which it is exposed to flames of the gas burner, fair experience and expertness are needed to this end. This is because the gas burner heating is a difficult work such that a gold layer in the noble metal foil layer is molten and case in between 8-10 folds formed on the pressed metal foil or the metal coping to complete it.

SUMMARY OF THE INVENTION

The present invention has been accomplished so as to considerably eliminate the limits imposed upon, or the problems arising in connection with, the fitness accuracy and thickness of the inner crown, when making the composite-layered crown for the restoration of crowns using such a metal casting or foil as mentioned above for the inner crown thereof. According to the present invention, it has been found that when an inner crown composed mainly of a noble metal is made for the composite-layered crown, satisfactory results are obtained by forming thick deposits on the inner crownforming surface of the working model of the tooth on which the state of the tooth to be restored is reproduced by using direct electroplating, instead of using a metal casting or foil, and, thereafter, removing the working model of the tooth.

In general, however, since the working model of the tooth on which the state of a tooth is reproduced is formed of a non-conductive material such as gypsum or synthetic resin, it is impossible to apply direct electroplating to the position to make an inner crown electroplate on a working model of a tooth. Moreover, since the inner crown of the composite-layered crown is used in a special environment defined as in the mouth, it should be formed primarily of a tarnish-, rust- or toxicity-free noble metal. However, when noble metals save gold and silver are electroplated with a D.C. plating, the deposited crystals occlude a hydrogen gas during electroplating. As a result, the metal deposits may peel off or crack due to deteriorations of the physical properties thereof, thus making thick deposition impossible. Additionally, the thickness of the metal layer to be plated is not uniform and is very thin in the concave form. Especially in the case of the working model of the tooth having usually at least one concave face, it is impossible to apply thereon uniform thick-deposits composed mainly of a noble metal.

According to the present invention, it has now been found that such problems can be solved by applying and solidifying a conductive coating material undissolvable in a plating bath on the working model of the tooth on which the state of a tooth is reproduced, even though it is formed of a non-conductive material such as gypsum or synthetic resin, thereby permitting the thus coated portion to be used as the cathode, and substituting a pulse plating for the D.C. plating which has heretofore been used for making an inner crown composed mainly of thick noble metal deposits layer, thereby passing a pulse current between anode and cathode at a given pulse width and a given pulsed current density and in a given duty cycle [(pulse on-time)/(pulse on-time) +(pulse off-time)]. In addition, the problem that only thin metal deposits are obtained on the concave application face can be solved by fixedly immersing an auxiliary electrode formed of the same metal as the metal to be plated in the plating bath between anode and cathode, while its one end is or is not connected to the anode and its other end if opposite and adjacent to a recess in said cathode.

More specifically, the present invention provides a method for making an inner crown of a composite-layered crown for the restoration of crowns, said inner crown being composed mainly of a noble metal, wherein an electrically conductive coating material undissolvable in a plating bath is applied and solidified on an inner crown-forming surface of a working model of a tooth on which the state of the tooth to be restored is reproduced and which is formed of a non-conductive material, and electrical connection is made so as to render said conductive coating material cathodic, while said coating material is immersed in said plating bath; an anode is immersed in said plating bath, while said anode is fixedly located on a position opposite to said inner crown-forming position; an auxiliary electrode formed of the same metal as the metal to be plated is immersed in said plating bath between said anode and said cathode, while its one end is or is not connected to said anode and its other end is opposite and adjacent to a recess in said cathode; and a pulse current is impressed between said anode and said cathode at a pulse width of 0.01 to 50 msec. and a pulsed current density of 1 to 20 $A/dm^2$ and in a duty cycle of 1 to 30 % for electroplating, thereby making said inner crown. The present invention also provides an apparatus for carrying out the aforesaid method.

BRIEF DESCRIPTION OF THE DRAWINGS

The method for making the inner crowns of the composite-layered crowns according to the present method and the apparatus for carrying out this method will now be explained in detail with reference to the accompanying drawings, which are given for the purpose of illustration alone, and in which.

DETAILED EXPLANATION OF THE PREFERRED EMBODIMENTS

Figure 1:
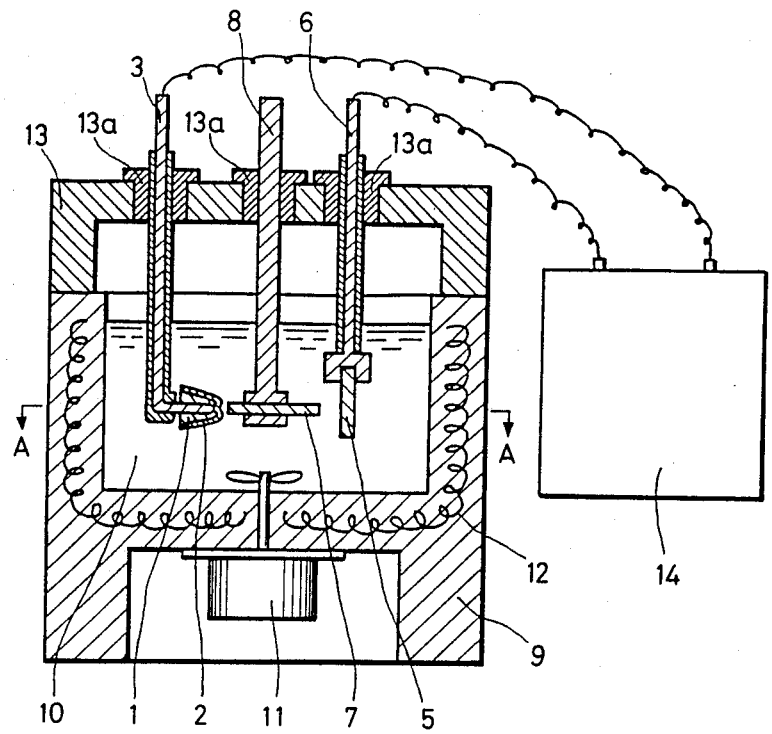
FIG. 1 is a view illustrating the structure of one embodiment of the apparatus for carrying out the method for making the inner crowns of the composite-layered crowns according to the present invention, and FIGS. 2 and 3 each are an enlarged end view taken along the A—A line of FIG. 1 to show another relationship between the working model of the tooth and an auxiliary electrode.
Figure 2:
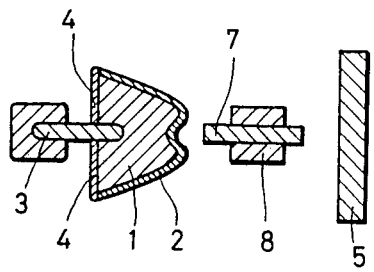
Figure 3:
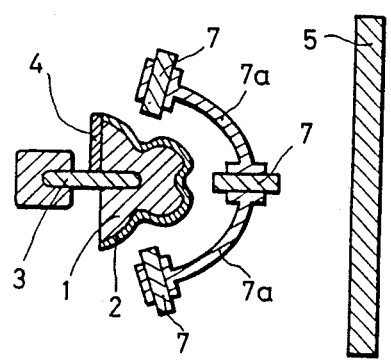

Referring to the drawings, there is shown a working model of a tooth 1 on which the state of the tooth to be restored is reproduced and which is formed of an electrically non-conductive material. As the non-conductive material, use may be made of any suitable material capable of easily reproducing the state of a tooth and being removed from an inner crown electroplated on an inner crown-forming surface position and made primarily of a noble metal without dissolving or damaging it such as, for instance, gypsum that is easily dissolvable by a gypsum dissolver manufactured by GC Dental Industrial Corp. and sold under the trade name of "RO-CLEAN" or synthetic acrylic, epoxy and ethyl silicate resins that are burned out upon heated, leaving behind the inner crown. The metal capable of forming an inner crown by electroplating is mainly a noble metal, and should be a noble metal which can be electroplated, and can securely and hygienically be applied under the conditions prevailing in the mouth such as, for instance, platinum, palladium, rhodium, ruthenium, gold and silver that may be used alone or in the form of alloys with iron, nickel, copper, cobalt, molybdenum, tungsten and/or indium. It is understood, however, that when porcelain is built up and fused on the inner crown for bonding thereonto, or a metal is bonded onto the inner crown by the lost-wax casting process, it is required to use a pure metal or its alloy that is unlikely to be softened and deformed at the fusing temperature of procelain and the casting temperature of the metal. An electrically conductive coating material 2 is applied and solidified on the inner crown-forming surface of the working model of a tooth 1 so as to use it as the cathode. The conductive coating material 2 should have the property of being not dissolved in a plating bath, and may comprise a combination of a binder, viz., cellulose resin, a mixed cellulose/methacrylate/phenolic resin or a mixed methacrylate/polystyrene resin with about 65 to 70 % of silver powders. A cathodic conducting material 3, which is insulated on its outside, is provided so as to fix and retain the working model of a tooth 1 in place and pass a current through the coating material 2 applied and solidified on the surface of the working model of a tooth 1 to render it cathodic. The cathodic conducting material 3 may extend through the working model of a tooth 1 from its side opposite to the inner crown-forming side, and be exposed at its end on that inner crown-forming side to pass a current through the coating material 2, or may be only embedded and fixed on the side of the working model of a tooth 1 which is opposite to the inner crownforming side. In the latter arrangement, an auxiliary conducting material 4 is needed so as to make electrical connection between end of the coating material 2 opposite to the inner crown-forming side and cathodic conducting material 3. Preferably, the auxiliary conducting material 4 should be insulated on its outer face. When the non-conducting working model of a tooth 1 is formed of gypsum, it is preferred that the working model of a tooth 1 is insulated on the surface area except for the inner crown-forming portion so as to prevent the elution of calcium ions from the gypsum in the plating bath (to be described later), which otherwise results in plating defects. Thus, the provision of such an insulation should preferably be performed simultaneously with the provision of an insulation on the the auxiliary conducting material 4. An anode 5 is held by an anodic conducting material 6 which is insulated on its outer face, and may be formed of the same material as the metal to be plated, or a material which does not elute in the plating bath such as, for instance, carbon. An auxiliary electrode 7 formed of the same metal as the metal to be plated may or may not be connected at its one end to the anode 5, and is held by a holding member 8 of an insulating material between cathodic conducting coating material 2 and anode 5 in the plating bath in such a manner that its other end is opposite and adjacent to a recess in the inner crown-forming position of the nonconductive working model of a tooth 1, i.e., a recess in the cathodic conducting coating material 2. The non-conductive working model of a tooth 1 on which the conductive coating material 2 is applied and solidified as the cathode, the anode 5 and the auxiliary electrode 7 are immersed in a plating bath 10 contained in a plating tank 9. The plating bath 10 contained in the plating tank 9 is mechanically stirred by an agitator 11. The plating bath 10 contained in the plating tank 9 is maintained at the predetermined temperature by a heater 12. A supporting member 13 for supporting and fixing the aforesaid cathodic conducting material 3, anodic conducting material 6 and auxiliary electrode-supporting member 8 is located above the plating tank 9, and should preferably include supporting and fixing means 13a formed of a rubber or springy material for holding their associated conducting materials 3, 6 and 8 in order to freely adjust the heights thereof in the plating bath 10. A power source device 14 is provided to impress a pulse current between anode 5 and cathodic coating material 2 at a pulse width of 0.01 to 50 msec. and a pulsed current density of 1 to 20 A/dm$^2$ and in a duty cycle of 1 to 30 %.

In order to carry out the method for making the inner crown of the composite-layered crown according to the present invention with the present apparatus of such a structure for the purpose of making the inner crown of the composite-layered crown, the non-conductive working model of a tooth 1, on which the state of the tooth to be restored has been reproduced, is firstly formed of a non-conductive material such as gypsum. Then, the anodic conducting material 6 (which has the anode 5 retained by the supporting and fixing means 13a on the supporting member 13 located above the plating tank 9) and the nonconductive working model of a tooth 1 (on which the state of the tooth to be restored is reproduced and which has the conductive coating material 2 applied and solidified on its inner crown-forming surface) are fixed and held in place, and the cathodic conducting material 3 (which is provided to pass a current through said conductive coating material 2 so as to make it cathodic, and is provided with an insulation on its outer face) and the auxiliary electrode-holding member 8 (which is formed of an insulating material and adapted to hold the auxiliary electrode 7—having its one end connected, or not connected, to the anode 5 and formed of the same metal as the metal to be plated—at the position where its other end is opposite and adjacent to the recess in the inner crown-forming surface of the nonconductive working model of a tooth 1). Subsequently, the nonconductive working model of a tooth 1, the anode 5 and the auxiliary electrode 7 are fixedly immersed in the plating bath 10 contained in the plating tank 9 including the agitator 11 for mechanically stirring the plating bath 10 and the heater 12 for maintaining the plating bath 10 at the predetermined temperature. Thereafter, the power source device 14 is actuated to apply a pulse current between the cathodic conducting material 3 and the anodic conducting material 6 at a pulse width of 0.01 to 50 msec. And a pulsed current density of 1 to 20 A/dm$^2$ and in a duty cycle of 1 to 30 % for electroplating.

Reference will then be made to the reasons for the application of such electroplating conditions. Since the less the pulse width, the easier it is to obtain the smooth surface of the deposited metal comprising finer grains, the lower limit of the pulse width is limited to 0.01 msec. that is the minimum value obtainable with a commercially available pulse power source. On the other hand, the upper limit of the pulse width is limited to 50 msec., since the grains on the surface of the deposited metal are so coarse at a pulse width exceeding 50 msec. that it loses its metallic gloss and becomes blackish. In a duty cycle below 1 %, on the one hand, the rate of deposition of the metal is usually low, and in a duty cycle exceeding 30 %, on the other hand, the off-time effects of the pulse current upon reductions in the amount of impurities in the deposited metal and reductions in the porosity of the deposited metal are so limited that the surface of the deposited metal becomes blackish. Thus, the duty cycle applied is limited to the range of 1 to 30 %. In general, as the pulsed current density increases, the rate of occurrence of crystal nucleus is relatively higher than the rate of growth of grains. The grains then become so fine that the surface of the deposited metal becomes smooth. However, when it is intended to obtain thick deposits having a thickness of the order of 40 to 300 micrometers, the rate of deposition of the metal is low at a density below 1 A/dm$^2$, while some phenomenones such as tarnish, cracking and peeling-off occur at a density exceeding 20 A/dm$^2$. Thus, the pulsed current density applied is limited to the range of 1 to 20 A/dm$^2$.

While the present invention has been described with reference to one embodiment wherein one non-conductive working model of a tooth 1 is fixedly immersed in the plating bath 10, two or more non-conductive working models 1 may be used, if required. Further, when two or more recesses are formed in the inner crown-forming position of one non-conductive working model 1, the corresponding number of auxiliary electrodes 7 may be located at the positions opposite and adjacent to said recesses. In this arrangement, however, only one auxiliary electrode-holding member 8 formed of an insulating material may be used, while a plurality of the auxiliary electrodes 7 may be connected with each other by means of insulating connector members 7a.

EXAMPLES

EXAMPLE 1

Provided was the non-conductive working model of the tooth 1 formed of gypsum, on which the state of the Upper first premolar to be restored was reproduced. One layer of the conductive coating material 2, which contained a cellulose resin/epoxy resin binder with 65 % by weight of silver powders and the viscosity of which was regulated with ethyl acetate, was applied and solidified on the inner crown-forming surface position of the working model of the tooth 1 to a thickness of about 10 micrometers by means of a brush. While electrical connection was made with the conductive coating material 2 as the cathode, it was fixedly immersed in the plating bath 10. While the anode 5 formed of a palladium plate of 15 mm in length, 15 mm in width and 1.5 mm in thickness was immersed in the plating bath 10, it was fixedly located at a position opposite to the inner crown-forming position of the working model of the tooth 1. The auxiliary electrode 7 formed of a palladium round rod of 2.5 mm in outer diameter and 20 mm in length was then inserted in the plating bath 10 between cathodic conducting coating material 2 and anode 5, while its one end was spaced away from the anode 5 by 20 mm and its other end was opposite and adjacent to the recess in the cathodic conducting coating material 2 but spaced away therefrom by 5 mm. Electroplating was carried out with the following plating bath composition under the following plating conditions.

Plating Bath Composition

PdCl$_2$ . 2H$_2$O: 3.7 g/l
Na$_2$HPO$_4$: 100 g/l
(NH$_4$)$_2$HPO$_4$ . 12H$_2$O: 20 g/l
Benzoic Acid (C$_7$H$_6$O$_2$): 2.5 g/l
pH: 9 or less
Bath Temperature: approx. 50° C.

Plating Conditions

Pulse Width: 0.1 msec.
Duty Cycle: 10 %
Pulsed Current Density: 4.3 A/dm$^2$
Plating Time: 10 hours After the completion of plating, the working model of the tooth 1 was immersed in a gypsum dissolver "ROCLEAN" (brand name) manufactured by G-C Dental Industrial Corp. and dissolved with an ultrasonic cleaner. Subsequently, it was washed with acetone, dilute nitric acid and water to remove the conductive coating material 2, and dried. As a result, a 70 micrometer-thick palladium inner crown of a shape well-fitted for the composite-layered crown could be made.

EXAMPLE 2

Provided was the non-conductive working model of the tooth 1 formed of gypsum, on which the state of the Lower first molar and the Upper central incisor to be restored were reproduced. One layer of the conductive coating material 2, which contained a cellulose resin binder with 65 % by weight of silver powders and the viscosity of which was regulated with ethyl acetate, was applied and solidified on the inner crown-forming surface of the working model of the tooth 1 to a thickness of about 20 micrometers by means of a brush. While electrical connection was made with the conductive coating material 2 as the cathode, it was fixedly immersed in the plating bath 10. While the anode 5 formed of a platinum plate of 10 mm length, 5 mm in width and 1 mm in thickness was immersed in the plating bath 10, it was fixedly located at a position opposite to the inner crown-forming position of the working model of the tooth 1. The auxiliary electrode 7 formed of a platinum flat plate of 3 mm in width, 1 mm in thickness and 25 mm in length was then inserted in the plating bath 10 between the cathodic conducting coating material 2 and the anode 5, while its one end was spaced away from the anode 5 by 5 mm and its other end was opposite and adjacent to the recess in the cathodic conducting coating material 2 but spaced away therefrom by 15 mm. Electroplating was carried out with the following plating bath composition under the following plating conditions.

Plating Bath Composition

Ammonium Phosphaste [(NH$_4$)$_2$HPO$_4$]: 20 g/l
Sodium Phosphate (Na$_2$HPO$_4$): 100 g/l
Platinum Chloride (PtCl): 4 g/l
pH: 9 or less
Bath Temperature: approx. 80° C Plating Conditions Pulse Width: 1 msec.
Duty Cycle: 20 %
Pulsed Current Density: 4.0 A/dm$^2$
Plating Time: 9 hours After the completion of plating, the working model 1 was immersed in a gypsum dissolver "ROCLEAN" (brand name) manufactured by G-C Dental Industrial Corp., and dissolved with an ultrasonic cleaner. Subsequently, it was washed with acetone, dilute nitric acid and water to remove the conductive coating material 2, and dried. As a result, a 60 micrometer-thick platinum inner crown of a shape well-fitted for the composite-layered crown for the First molar and Central incisor could be made.

EFFECTS OF THE INVENTION

The composite-layered crown for the restoration of crowns according to the present invention, as detailed above, has the following advantages over the prior art composite-layered crown in which a metal casting is used for the inner crown.

(1) Since the inner crown is made by forming noble metal deposits directly on the working model of a tooth by electroplating, it is well fit with the working model of a tooth without being affected by dimensional changes in the wax pattern, investment and cast alloy.

(2) An inner crown thickness of 40 to 400 micrometers can be obtained without causing any casting defects such as rounded, cold shut, rough surface and micro shrink. Accordingly, since the amount of porcelain or plastics to be built up on the inner crown can be increased to make the associated outer crown, it is possible to impart to the composite-layered crown the same configuration and color tone as those of a natural tooth. Further, since the a mount of a patient's tooth to be removed can be limited to a minimum in the tooth preparation for fixed prosthodontics, the time required for the tooth preparation for fixed prosthodontics can be curtailed from the dentist's standpoint, while the pain can be relieved for the patient.

(3) The inner crown can be made without recourse to a succession of works involving the preparation, investment and burning-out of wax patterns, casting and the polishing of castings. Thus, only by placing on a plating device the working model of a tooth on which one layer of a pasty conductive coating material has been applied, the inner crown can be made without relaying upon any seccessive works.

The composite-layered crown of the present invention has the following advantages over the prior art composite-layered crowns obtained by using a metal foil for their inner crowns.

(1) Since the inner crown can be made by forming noble metal deposits directly on the working model of a tooth by electroplating, it is much more fit with the working model of a tooth than a pressed metal foil or a metal coping obtained by covering a noble metal foil over the working model of a tooth and repeatedly pressing it against the working model of a tooth along the surface thereof.

(2) Since there is no need of swaging a pressed metal foil or a metal coping pressed against a working model of a tooth by means of a swager, the working model of a tooth may not break down in dependence upon type, configuration and size of the working model of a tooth or how to use a swager.

(3) No attention need be paid to the tooth preparation for fixed prosthodontics so as to facilitate the removal of the pressed metal foil or the metal coping from the working model of a tooth. Hence, the tooth preparation can freely be carried out.

(4) Further, there is no need of melting the metal in a noble metal foil layer and casting it in-between folds on a pressed metal foil or a metal coping.

Additionally, with the present invention, it is possible to solve the problems arising when making the inner crown—composed mainly of a noble metal—of the composite-layered crown by applying thick deposits on the inner crown-forming position of the working model of a tooth, on which the state of a tooth is reproduced, by direct electroplating.

(1) Since the working model of a tooth having the state of a tooth reproduced thereon is formed of a non-conductive material such as gypsum or synthetic resin, it is impossible to use it as the cathode for electroplating. However, this problem can be solved by applying and solidifying a conductive coating material undissolvable in the plating bath on the inner crown-forming surface of the non-conductive working model of a tooth, and using said coating material as the cathode.

(2) Since the inner crown of the composite-layered crown is used in the mouth, it should be composed mainly of a tarnish-, rust- or toxicity-free noble metal. Accordingly, when electroplating is applied, the deposited metal becomes so brittle due to its hydrogen absorptivity. However, this problem can be solved by using a pulse power source as the power source and impressing a pulse current between the anode and the cathode at a given pulse width and a given pulsed current density combined with a given duty cycle, i.e., at a pulse width of 0.01 to 50 msec. and a pulsed current density of 1 to 20 A/dm$^2$ and in a duty cycle of 1 to 30 %, for electroplating.

(3) In general, only thin metal deposits are obtained on an application face in the concave form, since the metal to be plated does not well spread thereover. However, this problem can be solved by fixedly immersing an auxiliary electrode formed of the same metal as the metal to be plated in the plating bath between the anode and the cathode, while its one end is or is not connected to the anode and its other end is opposite and adjacent to a recess in the cathode.

Further, the apparatus as claimed, described in details in the present disclosure and illustrated in the accompanying drawings, is so simple in the structure that it can easily be manufactured at lower costs. With the present apparatus, it is possible to efficiently carry out the present method for making the inner crown of the composite-layered crown. Thus, the present invention makes a great contribution to dentistry.

What is claimed is:

1. A method for making an inner crown of a composite-layered crown for the restoration of crowns, said inner crown being composed mainly of a noble metal, comprising the steps of: applying and solidifying an electrically conductive coating material undissolvable in a plating bath on an inner crown-forming surface on a working model of a tooth on which the state of the tooth to be restored is reproduced and which is formed of a non-conductive material, making an electrical connection so as to render said conductive coating material cathodic while said working model of a tooth with said coating material is immersed in said plating bath; immersing an anode in said plating bath while said anode is fixedly located on a position opposite to said inner crown-forming surface; immersing and fixing an auxiliary electrode having one end and formed of the same metal as the metal to be plated in said plating bath between said anode and said cathode, while an other end of said auxiliary electrode is opposite and adjacent to a recess in said cathode; and impressing a pulse current between said anode and said cathode at a pulse width of 0.01 to 50 msec. and a pulsed current density of 1 to 20 A/dm$^2$ and in a duty cycle of 1 to 30% for electroplating, thereby making said inner crown.

2. A method as defined in claim 1, wherein the thickness of deposits is 40 to 300 micrometers.

3. A method as defined in claim 1 or 2, wherein the metal to be plated is any one of platinum, palladium, rhodium, ruthenium, gold and silver.

4. A method as defined in claim 1 or 2, wherein the metal to be plated is an alloy of any one of noble metals of platinum, palladium, rhodium, ruthenium, gold and silver with one or more of iron, nickel, copper, cobalt, molybdenum, tungsten and indium.

5. A method as defined in any one of claims 1 to 2, wherein only one auxiliary electrode is used.

6. A method as defined in any one of claims 1 to 2, wherein two or more auxiliary electrodes are used.

7. A method as defined in any one of claims 1 to 2 wherein said one end is connected to said anode.

8. A method as defined in any one of claims 1 to 2 wherein said one end is not connected to said anode.

9. An apparatus for making an inner crown of a composite-layered crown for the restoration of a crown, comprising in combination:

a plating tank (9) containing a plating bath (10) and provided with an agitator (11) for mechanically stirring said plating bath (10) and a heater (12) for maintaining said plating bath (10) at a given temperature;

an anodic conducting material (6) for holding an anode (5), which is insulated on its outer face;

a cathodic conducting material (3) for fixing and holding in a fixed position a working model of a tooth (1) of a non-conductive material on which the state of the tooth to be restored is reproduced and which has an conductive coating material (2) applied and solidified on its inner crown-forming surface and for passing a current therethrough so as to make said coating material (2) cathodic, said cathodic conducting material (3) be insulated on its outer face;

an auxiliary electrode (7) formed of the same metal as the metal to be plated and having with its one end, and an auxiliary electrode-holding member (8) formed of an insulating material for holding said auxiliary electrode (7) between said conductive coating material (2) and said anode (5), while the other end of said auxiliary electrode (7) is opposite and adjacent to a recess in said inner crown-forming position of said working model of a tooth (1), and a supporting member (13) located above said plating tank (9) for holding and fixing said auxiliary electrode (7) and said electrode-holding member (8) in place; and a power source device (14) for passing a pulse current between said cathodic conducting material (3) and said anodic conducting material (6) at a pulse width of 0.01 to 50 msec. and a pulsed current density of 1 to 20 A/dm$^2$ and in a duty cycle of 1 to 30 %.

10. An apparatus as defined in claim 9, wherein said cathodic conducting material (3) extends through said working model of a tooth (1) from its side opposite to said inner crown-forming surface, and is exposed at one end on said inner crown-forming surface of said working model of a tooth (1).

11. An apparatus as defined in claim 9, wherein said cathodic conducting material (3) is fixed on the side of said working model of a tooth (1) opposite to said inner crown-forming surface thereof.

12. An apparatus as defined in any one of claims 9 to 11, wherein said supporting member (13) is provided with a holding and fixing means (13a) for freely varying the heights of said cathodic conducting material (3), said anodic conducting material (6) and said auxiliary electrode (8) in said plating bath.

13. An apparatus as defined in any one of claims 9 to 11 wherein said one end is connected to said anode.

14. An apparatus as defined in any one of claims 9 to 11 wherein said one end is not connected to said anode.

* * * * *